United States Patent
Tai et al.

(10) Patent No.: US 9,486,990 B2
(45) Date of Patent: Nov. 8, 2016

(54) METHOD FOR MANUFACTURING A SHAPED SHEET LAMINATE

(71) Applicants: Jung-Chi Tai, Tainan (TW); Ho-Hsi Yang, Tainan (TW); Chien-Chung Su, Tainan (TW)

(72) Inventors: Jung-Chi Tai, Tainan (TW); Ho-Hsi Yang, Tainan (TW); Chien-Chung Su, Tainan (TW)

(73) Assignee: KANG NA HSIUNG ENTERPRISE CO., LTD., Tainan (TW)

( * ) Notice: Subject to any disclaimer, the term of this patent is extended or adjusted under 35 U.S.C. 154(b) by 675 days.

(21) Appl. No.: 13/831,553

(22) Filed: Mar. 14, 2013

(65) Prior Publication Data

US 2014/0023822 A1   Jan. 23, 2014

(30) Foreign Application Priority Data

Jul. 18, 2012 (TW) .............................. 101125814 A

(51) Int. Cl.
| | |
|---|---|
| *A61F 13/15* | (2006.01) |
| *B32B 38/00* | (2006.01) |
| *B32B 3/12* | (2006.01) |
| *B32B 7/04* | (2006.01) |

(52) U.S. Cl.
CPC ..... *B32B 38/0012* (2013.01); *A61F 13/15699* (2013.01); *A61F 13/15731* (2013.01); *B32B 3/12* (2013.01); *B32B 7/045* (2013.01); *Y10T 156/1007* (2015.01); *Y10T 428/24149* (2015.01); *Y10T 428/24165* (2015.01)

(58) Field of Classification Search
None
See application file for complete search history.

(56) References Cited

U.S. PATENT DOCUMENTS

| | | | | |
|---|---|---|---|---|
| 4,260,443 A | * | 4/1981 | Lindsay | .................. A61F 13/02 156/220 |
| 7,468,114 B2 | * | 12/2008 | Sato | .................. A61F 13/15707 156/209 |
| 2010/0249740 A1 | | 9/2010 | Miyamoto et al. | |

FOREIGN PATENT DOCUMENTS

| | | |
|---|---|---|
| EP | 0 858 792 A2 | 8/1998 |
| EP | 0858792 A2 | 8/1998 |
| EP | 1 338 262 A1 | 8/2003 |
| EP | 1338262 A1 | 8/2003 |
| EP | 2 189 562 A1 | 5/2010 |
| EP | 2189562 A1 | 5/2010 |
| JP | 2004 113489 A | 4/2004 |
| JP | 2004113489 A | 4/2004 |

(Continued)

OTHER PUBLICATIONS

Extended European Search Report dated Oct. 17, 2013 corresponding to the related European Patent Application No. 13002071.2-1308.

(Continued)

*Primary Examiner* — Barbara J Musser
(74) *Attorney, Agent, or Firm* — DLA Piper LLP (US)

(57) ABSTRACT

There are provided a shaped sheet laminate that is adapted for an absorbent article and that has a specific structure to enhance the absorbing effect of the absorbent article, a method for manufacturing the shaped sheet laminate, and a shaping apparatus adapted to manufacture the shaped sheet laminate. The shaping apparatus includes a first roller having a rolling surface, a plurality of indentations that are indented from the rolling surface, a plurality of annular inner wall surfaces respectively defining the indentations, and a plurality of suction holes that are in air communication the respective indentations. Each of the annular inner wall surfaces has an annular outer edge that meets the rolling surface.

4 Claims, 12 Drawing Sheets

(56) References Cited

FOREIGN PATENT DOCUMENTS

| JP | 2006-175689 | 7/2006 |
| JP | 2007 167212 A | 7/2007 |
| JP | 2007167212 A | 7/2007 |
| JP | 2008-136561 | 6/2008 |
| JP | 2009-89965 | 4/2009 |
| JP | 2011-132623 | 7/2011 |
| JP | 2012 120882 A | 6/2012 |
| JP | 2012120882 A | 6/2012 |
| TW | 200924723 | 6/2009 |

OTHER PUBLICATIONS

Search Report issued to Taiwanese counterpart Application No. 101125814 on Mar. 23, 2015 (2 pages).

\* cited by examiner

METHOD FOR MANUFACTURING A SHAPED SHEET LAMINATE

CROSS-REFERENCE TO RELATED APPLICATION

This application claims priority of Taiwanese Application No. 101125814, filed on Jul. 18, 2012.

BACKGROUND OF THE INVENTION

1. Field of the Invention

The invention relates to a shaped sheet laminate, a method and a shaping apparatus for manufacturing the shaped sheet laminate.

2. Description of the Related Art

A commercial absorbent article such as a disposable diaper, a sanitary napkin and so forth usually includes a surface layer for contacting human skin and guiding fluids discharged from human body to keep human skin dry and comfortable. Referring to FIGS. 1 and 2, U.S. Patent Application Publication No. 2010/0249740 A1 discloses a shaped sheet laminate 1, which is adapted for an absorbent article as a surface layer and has an uneven surface structure. As shown in FIG. 1, the shaped sheet laminate 1 includes a plurality of indented portions 11, a plurality of projection portions 14, and a plurality of first and second connection portions 12 and 13. For further understanding the structure of the shaped sheet laminate 1, FIG. 2 is a pattern chart that depicts a six-point embossing pattern of the shaped sheet laminate 1 in a coordinate system, wherein $\alpha$ represents the indented portion 11, $\beta$ represents the projection portion 14, $\gamma$ represents the first connecting portion 13, and $\epsilon$ represents the second connecting portion 12. It is shown in FIGS. 1 and 2 that the indented portions 11 are separated from each other by respective projection portions 14 and first and second connecting portions 12 and 13, which results in weak fluid distribution between the indented portions 11 when the fluid is flowing on the indented portions 11, thereby reducing the absorbing effect of the absorbent article.

Further, the shaped sheet laminate 1 is manufactured using a first roller, a second roller, and a third roller cooperating with each other to bond a top sheet and a bottom sheet together, thus forming the shaped sheet laminate 1. The first roller is made of several parallel arranged on a rotating shaft, and the adjacent gears are combined such that their tooth pitches are offset by 0.5 pitch. The second roller has similar configuration with the first roller while gear teeth of the second roller mesh with those of the first roller. The third roller is in rolling contact with the first roller and capable of being heated. While manufacturing the shaped sheet laminate 1, the top sheet passes through a first nip zone defined by the first and second rollers to form a projection-indentation structure, followed by delivering the bottom sheet together with the top sheet to pass through a second nip zone between the first roller and the third roller, so as to bond the top sheet and the bottom sheet to form the shaped sheet laminate 1.

However, it is time consuming to assemble the first and second rollers, since the gears of the first and second rollers are required to remain in the specific configuration.

SUMMARY OF THE INVENTION

Therefore, one object of the present invention is to provide a method for manufacturing a shaped sheet laminate adapted for an absorbent article and having a specific structure to enhance the absorbing effect.

Accordingly, a method for manufacturing a shaped sheet laminate of the present invention includes the following steps:

(a) providing a first roller, a second roller, and a third roller, the first roller having a rolling surface, a plurality of indentations that are arranged in intersecting rows and that are indented inwardly from the rolling surface, a plurality of annular inner wall surfaces respectively defining the indentations, and a plurality of suction holes that are in air communication with the respective indentations and that are connected to a suction device, each of the annular inner wall surfaces having an annular outer edge that meets the rolling surface, the second roller having a rolling surface that is formed with a plurality of protrusion members thereon, the third roller having a rolling surface;

(b) feeding a top sheet to pass through a first nip zone formed between the first roller and the second roller, wherein each of the protrusion members extends into one of the indentations in the first nip zone, and the top sheet is pressed by the protrusion members and is sucked to contact against the annular inner wall surfaces through the suction holes and the suction device so that the top sheet is formed with a plurality of projection portions corresponding to the indentations of the first roller, and a plurality of indented annular connecting portions each surrounding one of the projection portions; and (c) subsequently feeding the top sheet together with a bottom sheet to pass through a second nip defined by the first roller and the third roller, wherein the third roller is heated so that the top sheet and the bottom sheet are melt bonded to each other between the rolling surfaces of the first and third rollers.

Another object of the present invention is to provide a shaping apparatus that is adapted for manufacturing shaped sheet laminates and that is relatively easy to assemble.

A shaping apparatus according to this invention includes:

a first roller having a rolling surface, a plurality of indentations that are arranged in intersecting rows and that are indented inwardly from the rolling surface, a plurality of annular inner wall surfaces respectively defining the indentations, and a plurality of suction holes that are in air communication with the respective indentations, each of the annular inner wall surfaces having an annular outer edge that meets the rolling surface; and a second roller disposed in rolling contact with the first roller to form a nip zone, the second roller having a rolling surface that is formed with a plurality of protrusion members thereon, each of the protrusion members extending into a respective one of the indentations in the nip zone.

Yet another object of the present invention is to provide a shaped sheet laminate adapted for an absorbent article and having a specific structure to enhance the absorbing effect.

Accordingly, a shaped sheet laminate of this invention includes:

a bottom sheet; and a top sheet laminated with the bottom sheet and having a plurality of indented annular connecting portions that are bonded to the bottom sheet, and a plurality of first projection portions, each of which is surrounded by one of the indented annular connecting portions, the indented annular connecting portions being arranged in intersecting rows.

BRIEF DESCRIPTION OF THE DRAWINGS

Other features and advantages of the present invention will become apparent in the following detailed description of the preferred embodiments with reference to the accompanying drawings, of which.

DETAILED DESCRIPTION OF THE PREFERRED EMBODIMENTS

Figure 1:
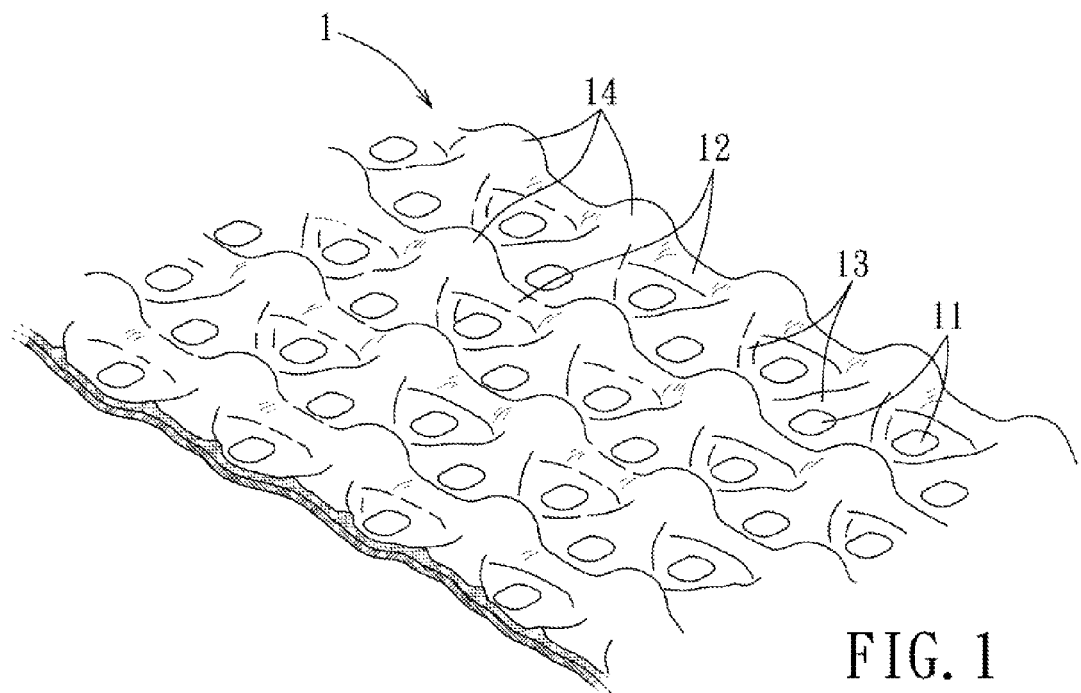
FIG. 1 is a fragmentary perspective view of a conventional shaped sheet laminate disclosed in US Patent Application Publication No. 2010/0249740 A1.

Before the present invention is described in greater detail, it should be noted that like elements are denoted by the same reference numerals throughout the disclosure.

Figure 8:
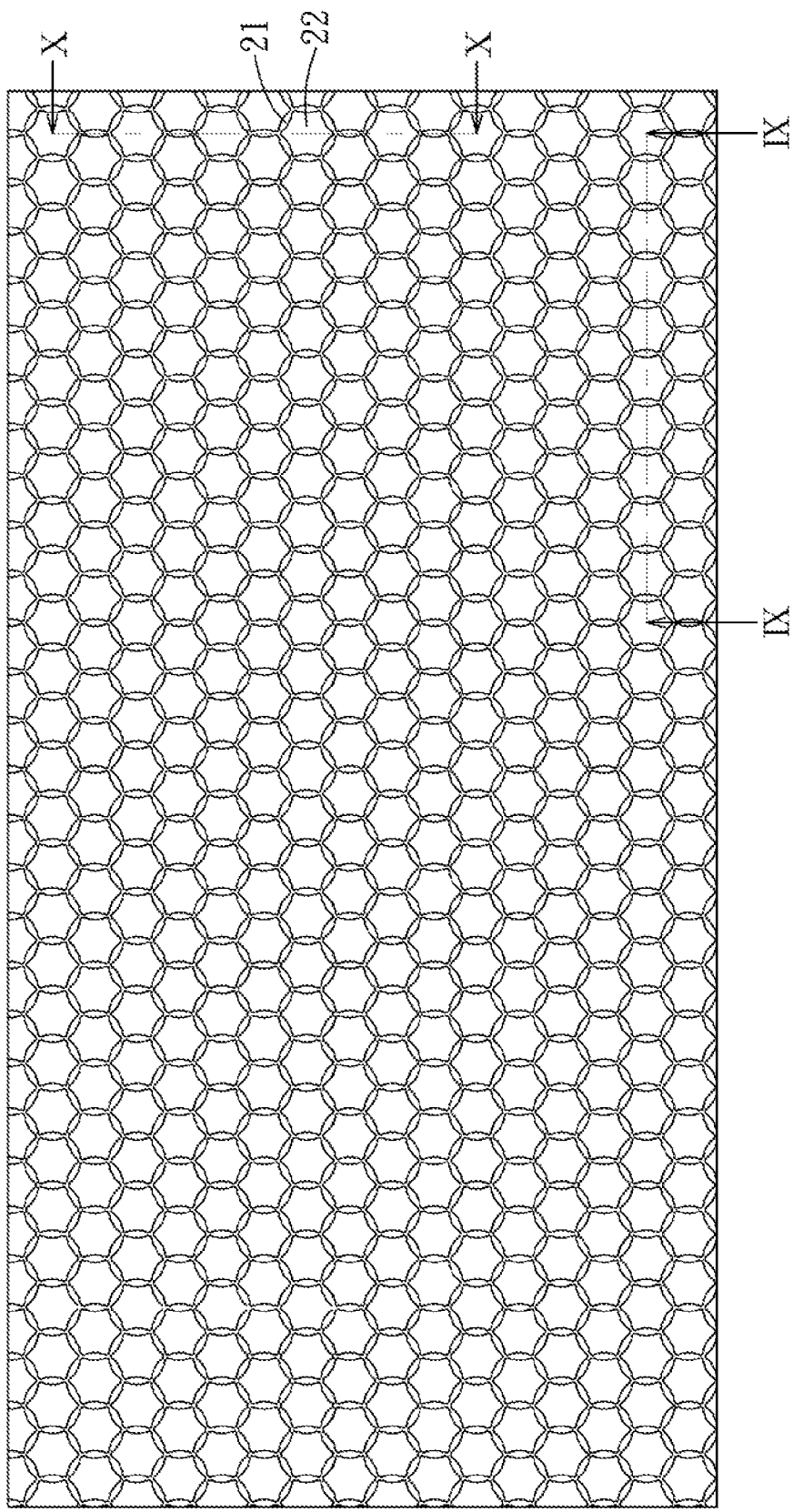
FIG. 8 is a top view of a shaped sheet laminate of the first preferred embodiment according to the present invention.
Figure 9:
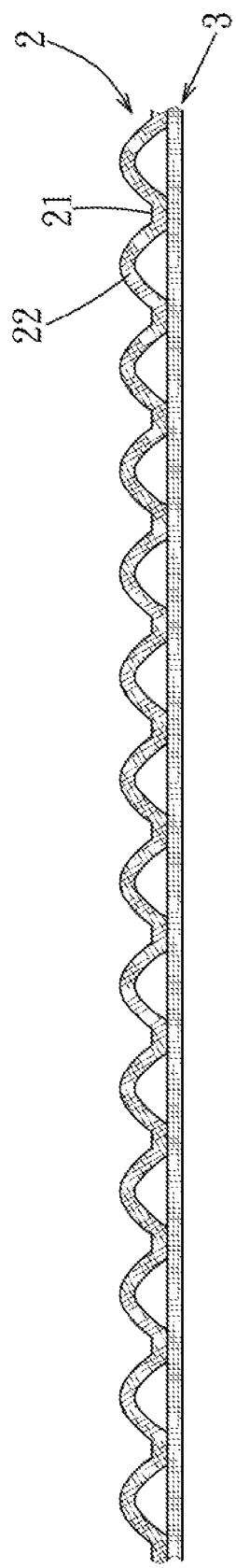
FIG. 9 is a fragmentary sectional view of the shaped sheet laminate taken along line IX-IX in FIG. 8.
Figure 10:
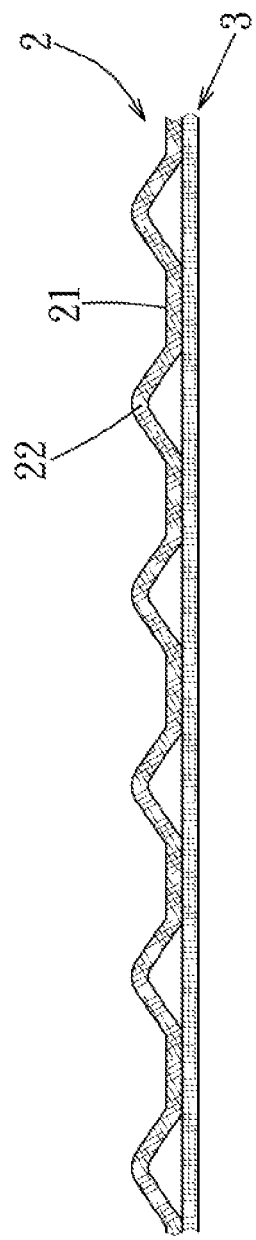
FIG. 10 is a fragmentary sectional view of the shaped sheet laminate taken along line X-X in FIG. 8.

Referring to FIGS. 3, 4, 5, 6, and 7, the first preferred embodiment of a method for manufacturing a shaped sheet laminate according to the present invention includes the following steps:

(a) providing a first roller 4, a second roller 5, and a third roller 6, the first roller 4 having a rolling surface 41, a plurality of indentations 42 that are arranged in intersecting rows and that are indented inwardly from the rolling surface 41, a plurality of annular inner wall surfaces 421 respectively defining the indentations 42, and a plurality of suction holes 43 that are in air communication with the respective indentations 42 and that are connected to a suction device 7, each of the annular inner wall surfaces 421 having a guiding surface 424 and an annular outer edge 423 that has a hexagonal shape and that meets the rolling surface 41, the second roller 5 having a rolling surface 51 that is formed with a plurality of protrusion members 52 thereon, the third roller 6 having a rolling surface 61;

(b) feeding a top sheet 2 to pass through a first nip zone 45 formed between the first roller 4 and the second roller 5, wherein each of the protrusion members 52 extends into one of the indentations 42 in the first nip zone 45, and the top sheet 2 is pressed by the protrusion members 52 and is sucked to contact against the annular inner wall surfaces 421 through the suction holes 43 and the suction device 7 so that the top sheet 2 is formed with a plurality of first projection portions 22 corresponding to the indentations 42 of the first roller 4, and a plurality of indented annular connecting portions 21 each surrounding one of the projection portions 22 in a hexagonal shape (see FIGS. 8, 9, and 10); and (c) subsequently feeding the top sheet 2 together with a bottom sheet 3 to pass through a second nip zone 46 defined by the first roller 4 and the third roller 6, wherein the third roller 6 is heated to a predetermined temperature ranging from 70° C. to 150° C. so that the top sheet 2 and the bottom sheet 3 are melt bonded to each other between the rolling surface 41 of the first roller 4 and the rolling surface 61 of the third roller 6, thereby obtaining the shaped sheet laminate of this preferred embodiment.

Figure 11:
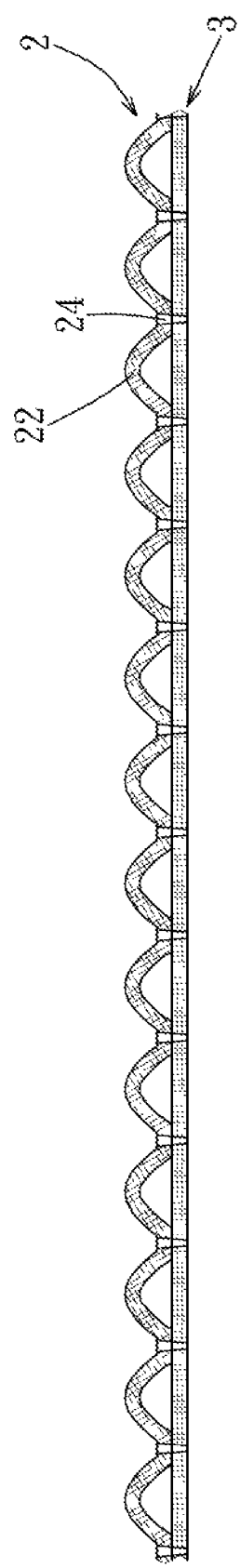
FIG. 11 is a fragmentary sectional view of a modification of the shaped sheet laminate of the first preferred embodiment, showing that the shaped sheet laminate further has a plurality of pin holes penetrating through a top sheet and a bottom sheet.

Preferably, in the step (a), a fourth roller 8 and a fifth roller 9 may be further provided. The fourth roller 8 has a rolling surface 81 that is formed with a plurality of spaced-apart pins 82 and that is heated to a predetermined temperature ranging from 70° C. to 150° C. The fifth roller 9 has an elastic rolling surface 91. In the step (c), the top sheet 2 and the bottom sheet 3, which have been bonded to each other, are fed to pass through a third nip zone 89 defined by the fourth roller 8 and the fifth roller 9, and the pins 82 extend through the top sheet 2 and the bottom sheet 3 in the third nip zone 89 to form a plurality of pin holes 24 in the indented annular connecting portions 21 (see FIG. 11).

Figure 3:
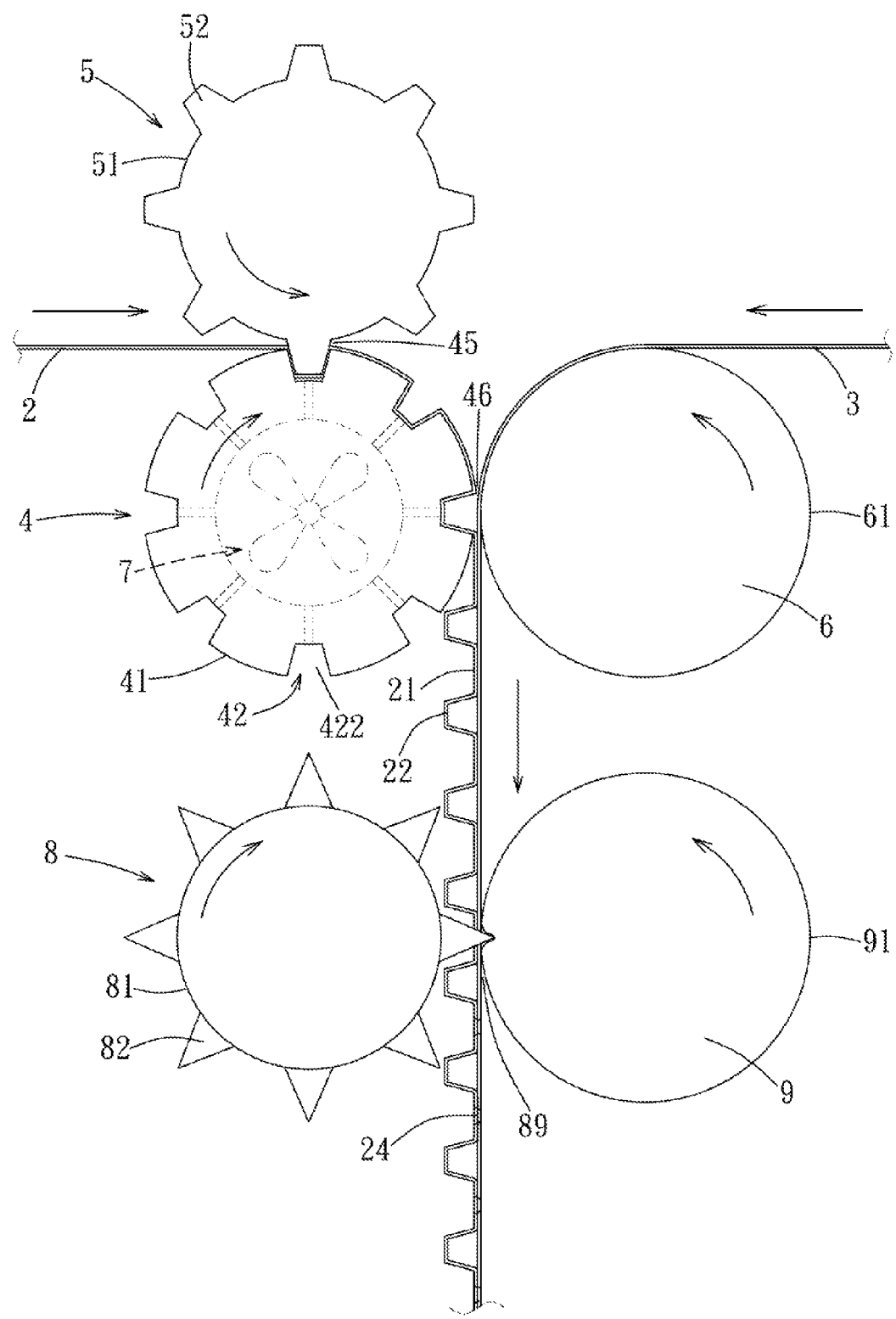
FIG. 3 is a schematic diagram illustrating a method for manufacturing a shaped sheet laminate of the first preferred embodiment according to this invention.
Figure 4:
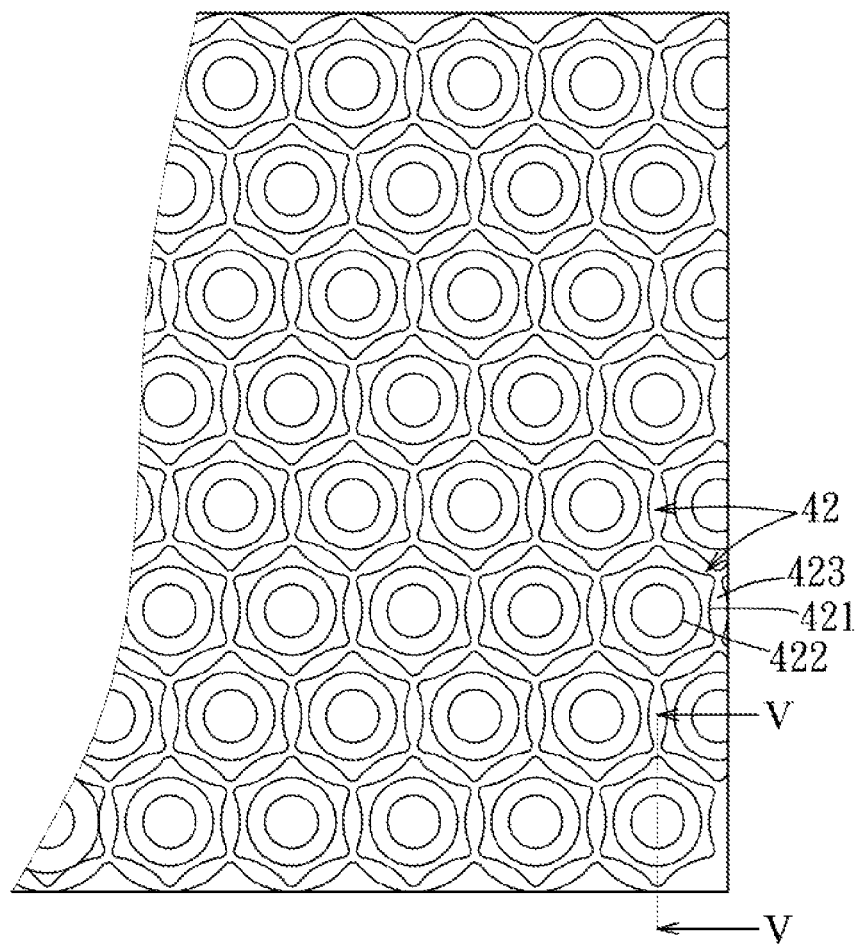
FIG. 4 is a fragmentary side view of a first roller of a shaping apparatus used in the first preferred embodiment according to the present invention.
Figure 5:
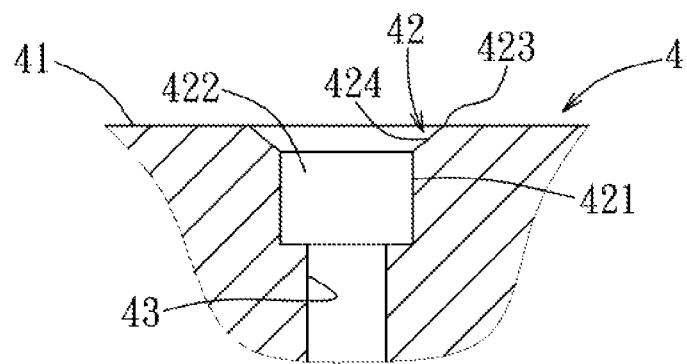
FIG. 5 is a cross sectional view taken along line V-V in FIG. 4.
Figure 6:
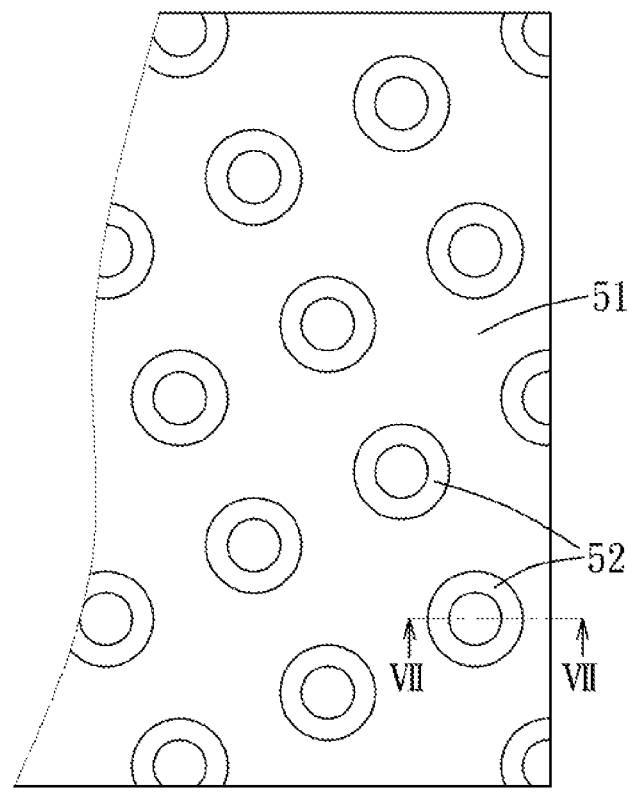
FIG. 6 is a fragmentary side view of a second roller of the shaping apparatus used in the first preferred embodiment according to the present invention.
Figure 7:
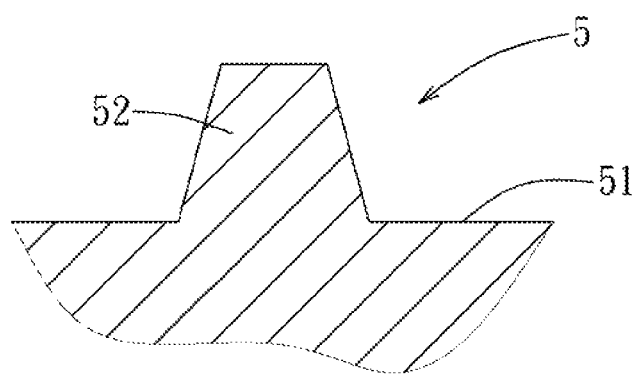
FIG. 7 is a fragmentary cross sectional view taken along line VII-VII in FIG. 6.

In this embodiment, each of the first roller 4 and the second roller 5 is formed integrally as one piece, thereby having a relatively stable structure and easy to be assembled. As shown in FIG. 3, the shaped sheet laminate according to the present invention can be applied to an absorbent article as a surface layer to be in contact with human skin. The absorbent article may be a disposable diaper, a sanitary napkin, or a panty liner. When a fluid discharged from human body flows downwardly along the projection portions 22 and accumulates on the indented annular connecting portions 21, the interconnecting structure of the indented annular connecting portions 21 of the top sheet 2 is capable of guiding and distributing the fluid quickly and effectively. The projection portions 22 of the shaped sheet laminate may keep the human skin away from the fluid thereby allowing human skin to maintain a relatively dry and comfortable state. Besides, the fluid may be absorbed downwardly through the bottom sheet 3 to an absorption layer (not shown) that is disposed under the shaped sheet laminate, or stored in spaces between the projection portions 22 and the bottom sheet 3, so as to prevent liquid from flowing back to a top surface of the top sheet 2 and causing leaking. Furthermore, the pin holes 24 formed in the shaped sheet laminate of this invention is used for guiding the fluid flowing faster through the shaped sheet laminate to reach the absorption layer (not shown) which is disposed under the shaped sheet laminate, thereby improving the absorption effect of the absorbent article.

Figure 12:
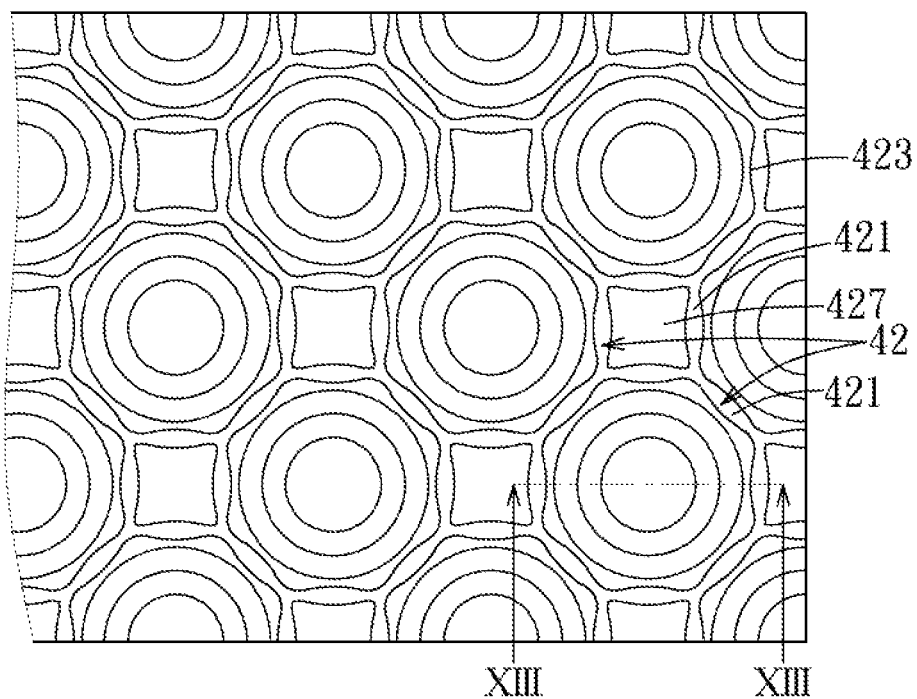
FIG. 12 is a fragmentary side view showing a first roller of a shaping apparatus of the second preferred embodiment according to the present invention.
Figure 13:
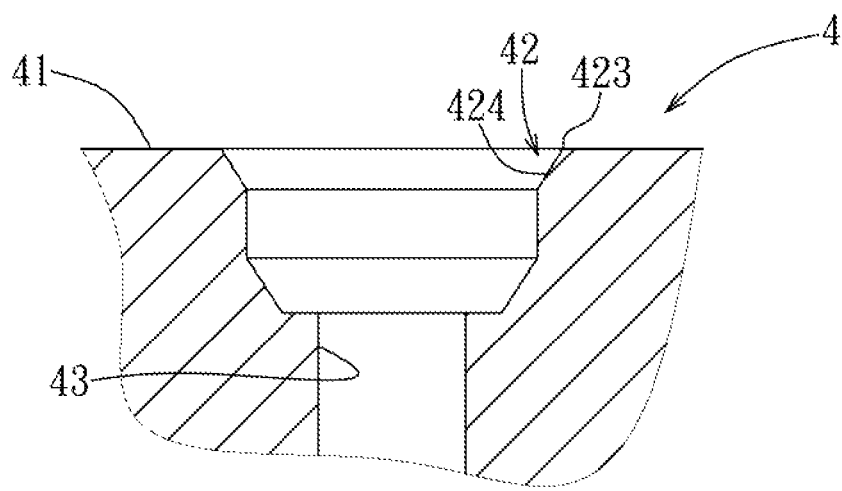
FIG. 13 is a fragmentary sectional view taken along line XIII-XIII in FIG. 12.
Figure 14:
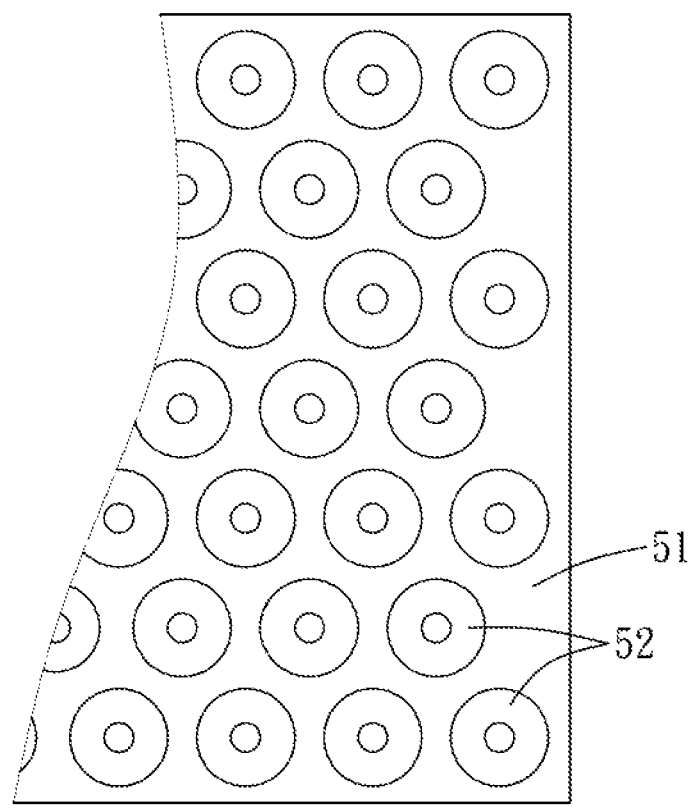
FIG. 14 is a fragmentary side view of a second roller of the shaping apparatus of the second preferred embodiment.

Referring to FIGS. 12, 13, and 14, the second preferred embodiment of the method for manufacturing the shaped sheet laminate according to the present invention has similar steps to those of the first embodiment. The main difference between this embodiment and the previous embodiment resides in the configuration of the first roller 4 of the shaping apparatus, and the structure of the top sheet 2 of the shaped sheet laminate. The annular outer edge 423 of each of the annular inner wall surfaces 421 has an octagonal shape, and the first roller 4 further has a plurality of second indentations 427 each having a maximum width that is smaller than that of each of the indentations 42 in a direction parallel to the top surface of the top sheet 2. In this embodiment, the second indentations 427 are arranged with the indentations 42 intersectingly in rows and columns.

Figure 15:
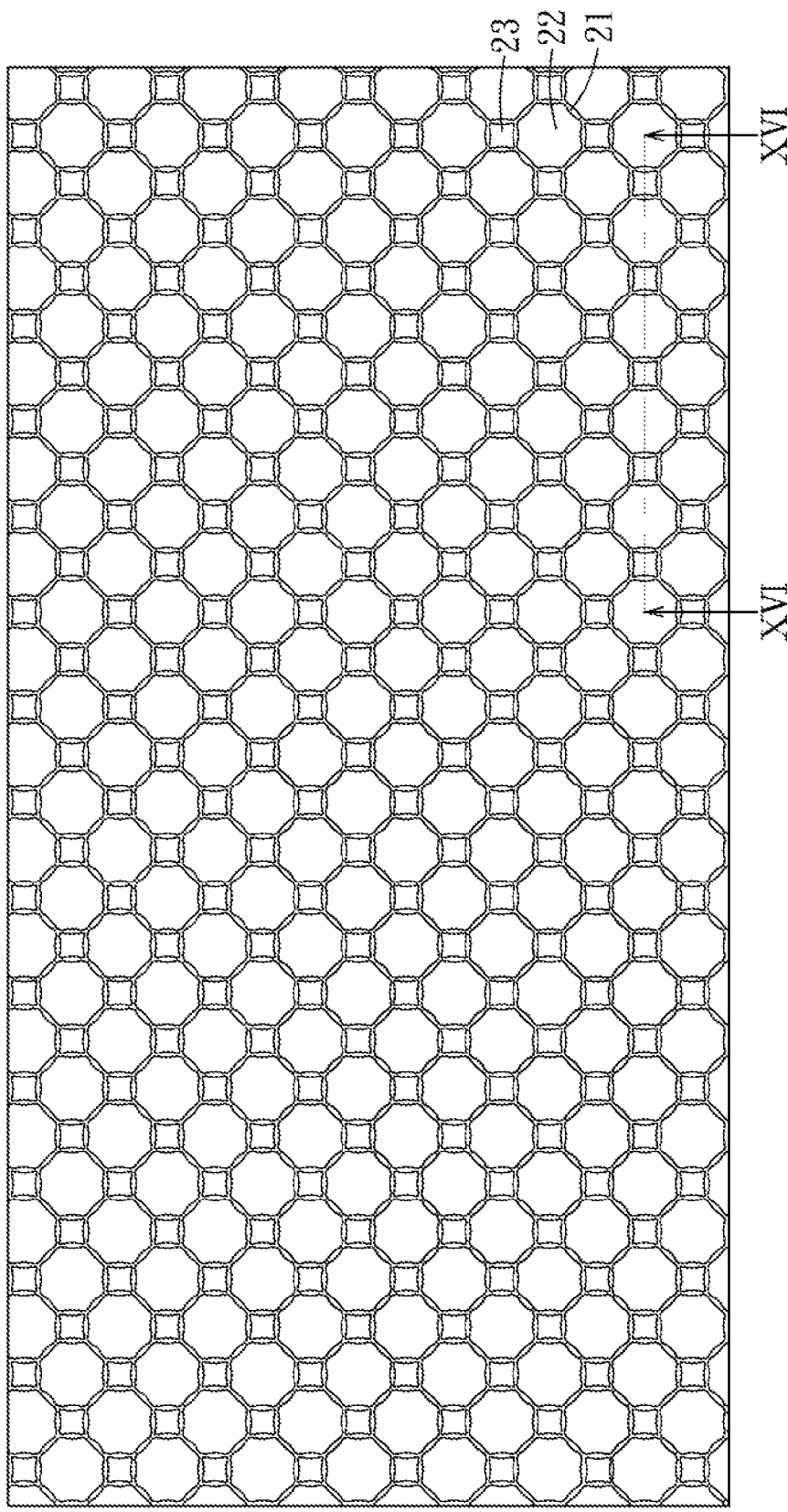
FIG. 15 is a top view of a shaped sheet laminate of the second preferred embodiment.
Figure 16:
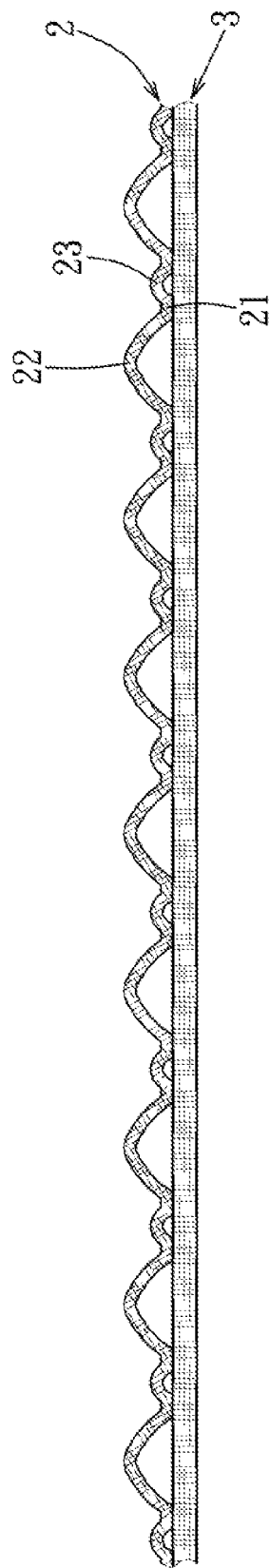
FIG. 16 is a fragmentary sectional view taken along line XVI-XVI in FIG. 15.
Figure 17:
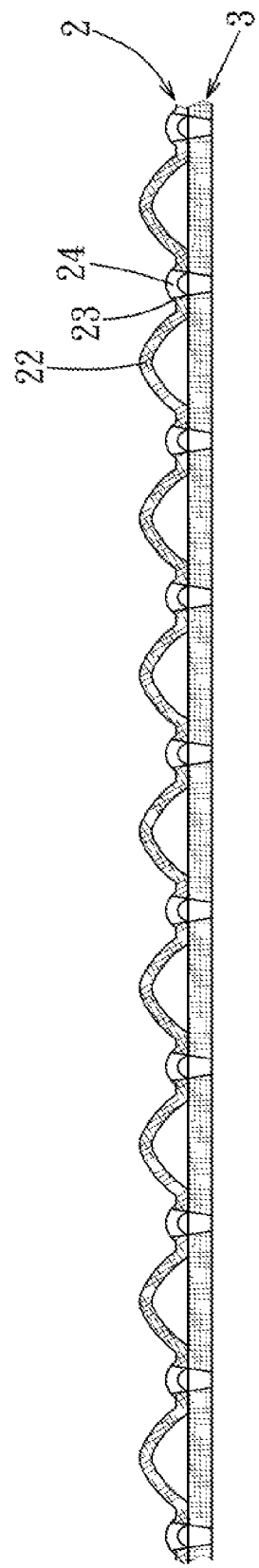
FIG. 17 is a fragmentary sectional view of a modification of the shaped sheet laminate of the second preferred embodiment, which has a plurality of pin holes penetrating through a top sheet and a bottom sheet.

As shown in FIGS. 15 and 16, each of the indented annular connecting portions 21 of the top sheet 2 of this embodiment forms an octagonal shape and has eight sides, and each of the indented annular connecting portions 21 shares four spaced apart ones of the sides respectively with four other ones of the indented annular connecting portions 21. The top sheet 2 of the shaped sheet laminate of this embodiment further includes a plurality of spaced-apart second projection portions 23 respective to the second indentations 427 of the first roller 4. Each of the second projection portions 23 is connected to and surrounded by four of the indented annular connecting portions 21. Similar to the first embodiment, the top sheet 2 of this embodiment may further have a plurality of spaced-apart pin holes 24 formed in, but not limited to, the respective second projection portions 23 (see FIG. 17), or in the indented annular connecting portions 21. The second preferred embodiment has the same advantages as those of the first preferred embodiment.

Figure 18:
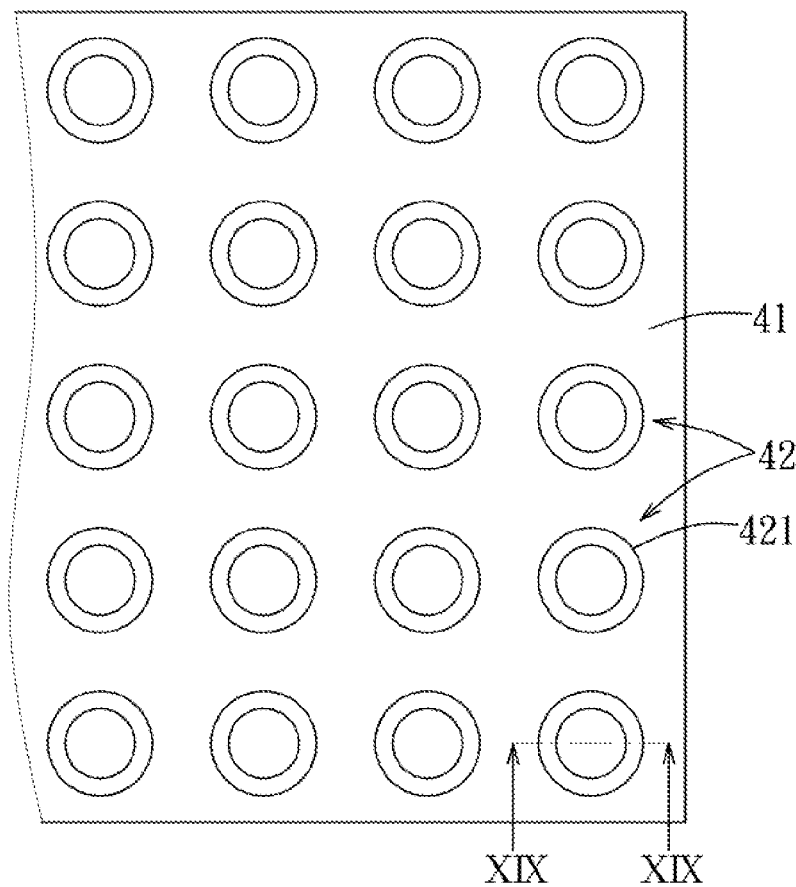
FIG. 18 is fragmentary side view of a first roller of a shaping apparatus of the third preferred embodiment of the present invention.
Figure 19:
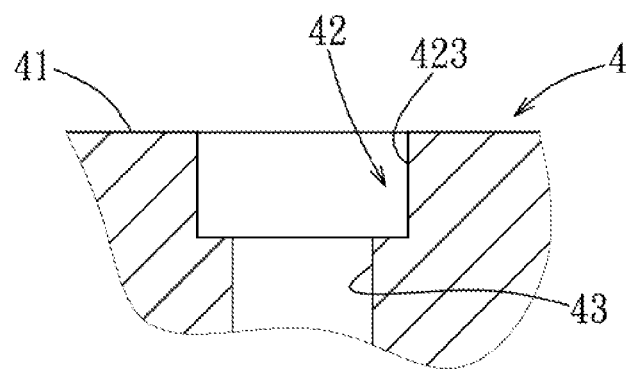
FIG. 19 is a fragmentary sectional view taken along line XIX-XIX in FIG. 18.

As shown in FIGS. 18 and 19, the third preferred embodiment of the method according to the present invention has steps similar to those of the first preferred embodiment. The main difference between this embodiment and the first preferred embodiment resides in that the annular outer edge 423 of each of the annular inner wall surfaces 421 of the first roller 4 has a circular shape, and each of the indented annular connecting portions of the top sheet of this embodiment forms a circular shape. The third preferred embodiment has the same advantages as those of the first preferred embodiment.

EXAMPLES

An absorbent article of each of the following Examples was prepared to include the second preferred embodiment of the shaped sheet laminate without the pin holes formed thereon, an absorbing layer laminated with and disposed under the shaped sheet laminate, and a bottom layer laminated with and disposed under the absorbing layer. The absorbing layer of each of the Examples was made from paper pulps and superabsorbent polymer (SAP) which are similar to the material of the absorbing layer in the Comparative Examples.

Example 1

For the shaped sheet laminate of an absorbent article of Example 1, each of the top sheet and the bottom sheet was made of a through-air bonded nonwoven fabric with a basis weight of 18 gsm. The sample length of the shaped sheet laminate of Example 1 was 215 mm.

Example 2

For the shaped sheet laminate of an absorbent article of Example 2, the top sheet was made of a through-air bonded nonwoven fabric with a basis weight of 18 gsm, and the bottom sheet was made of a thermal bonded nonwoven fabric with a basis weight of 35 gsm. The sample length of the shaped sheet laminate of Example 2 was 215 mm.

Example 3

For the shaped sheet laminate of an absorbent article of Example 3, the top sheet was made of a through-air bonded nonwoven fabric with a basis weight of 18 gsm, and the bottom sheet was made of a through-air bonded nonwoven fabric with a basis weight of 25 gsm. The sample length of the shaped sheet laminate of Example 3 was 215 mm.

Comparative Example 1

Figure 2:
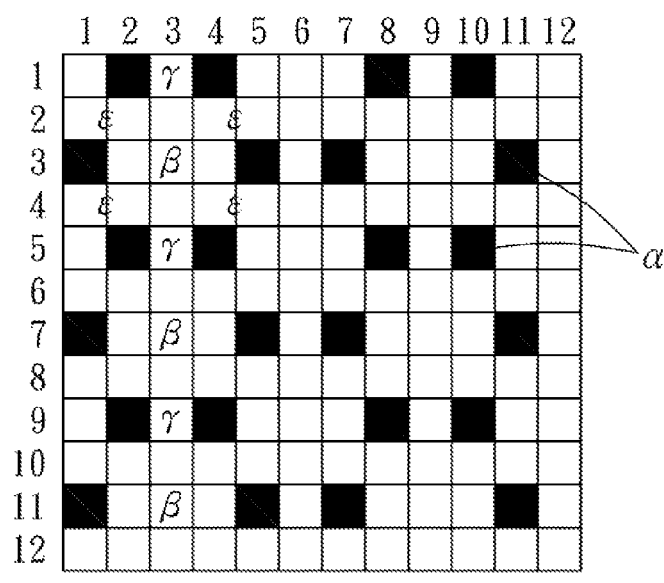
FIG. 2 is a pattern chart that depicts a six-point embossing pattern of the shaped sheet laminate in a coordinate system in US Patent Application Publication No. 2010/0249740 A1.

An absorbent article of Comparative Example 1 is a commercial diaper product (Merries, manufactured by Kao Corporation), which has the surface structure as shown in FIGS. 1 and 2. The sample length of the diaper product was 255 mm.

Comparative Example 2

An absorbent article of Comparative Example 2 was a commercial product of a sanitary napkin (Carnation, manufactured by Kang Na Hsiung Enterprise Co., Ltd.) and had a sample length of 215 mm. In the absorbent article of Comparative Example 2, the top sheet was made of a through-air bonded nonwoven fabric with a basis weight of 25 gsm, and the bottom sheet was made of a thermal bonded nonwoven fabric with a basis weight of 32 gsm. The top and bottom sheets were melt bonded to each other without projection portions formed thereon.

<Determinations of Leaking Quantity Under Load and Diffusion Property>

Procedures for measuring the leaking quantity under load and diffusion property of the absorbent article of each of the Examples and the Comparative Examples include the following steps:

1. preparing artificial menstruation blood having a viscosity of 7.3±0.2 cps and a density of 1.04±0.01 g/ml at room temperature (26±1° C.);

2. dripping dropwise 5 ml of the artificial menstruation blood onto a central area of the absorbent article of each of the Examples and Comparative examples using a burette to form a diffusion area on the absorbent article;

3. measuring the length of the diffusion area by a ruler to obtain the diffusion length of each of the Examples and the Comparative Examples;

4. applying a 2.0±0.1 kgw metal cuboid with an area of 200 mm×70 mm onto the central area of the absorbent article of each of the Examples and the Comparative Examples for 180±0.2 seconds, followed by removing and wiping the metal cuboid; and 5. weighting and placing several filter papers onto the central area of the absorbent article of each of the Examples and the Comparative Examples, applying the metal cuboid onto the filter papers for 30±1 seconds, removing the metal cuboid, and calculating and recording the increased weight of the filter papers so that the leaking quantity of each of the Examples and the Comparative Examples was obtained.

Results of leaking quantity and the diffusion property of the absorbent article of each of the Examples and the Comparative Examples are shown in Table 1.

<Measurement of Absorption Speed>

A procedure for measuring the absorption speed of the absorbent article of each of the Examples and the Comparative examples includes the following steps:

1. placing an absorption speed tester (manufactured by Kang Na Hsiung Enterprise Co., Ltd), which weighed about 480 grams, onto the central area of the absorbent article of each of the Examples and the Comparative Examples;

2. loading 15 ml of a Congo red solution into the absorption speed tester for delivering the solution onto the absorbent article of each of the Examples and the Comparative Examples and simultaneously counting the time until the Congo red solution was totally absorbed by the absorbent article, so as to obtain the absorption speed of the absorbent article of each of the Examples and the Comparative Examples. Results of the absorption speed are shown in Table 1.

TABLE 1

|  | Ex. 1 | Ex. 2 | Ex. 3 | Comp. Ex. 1 | Comp. Ex. 2 |
|---|---|---|---|---|---|
| Sample Length (mm) | 215 | 215 | 215 | 255 | 215 |
| Bulk Weight of shaped sheet laminate (g/pc) | 7.0 | 6.8 | 6.5 | 8.9 | 6.3 |
| Leaking Quantity under load (g) | 0.3 | 0.5 | 0.2 | 0.4 | 0.4 |
| Diffusion length (mm) | 46 | 45 | 43 | 44 | 52 |
| Absorption Speed (sec) | 7.42 | 7.20 | 6.35 | 12.88 | 18.53 |

From the results of the Examples, it is shown in Table 1 that the leaking quantity of the absorbent article of each of the Examples is in a range between 0.2 g and 0.5 g, and the diffusion length of the absorbent article of each of the Examples is in a range between 43 mm and 46 mm. Such results of the Examples reach the common standard of the commercial sanitary napkins. The results of absorption speed of the Examples (6.35 seconds to 7.42 seconds) are faster than those of the Comparative Examples (12.88 seconds and 18.53 seconds), which indicate the better absorption effect achieved in the Examples than in the Comparative Examples.

While the present invention has been described in connection with what are considered the most practical and preferred embodiments, it is understood that this invention is not limited to the disclosed embodiments but is intended to cover various arrangements included within the spirit and scope of the broadest interpretation so as to encompass all such modifications and equivalent arrangements.

What is claimed is:

1. A method for manufacturing a shaped sheet laminate that is adapted for an absorbent article, said method comprising the steps of:
    (a) providing a first roller, a second roller, and a third roller, the first roller being integrally formed as one piece and having a continuous rolling surface, a plurality of indentations that are arranged in intersecting rows and that are indented inwardly from the rolling surface, a plurality of annular inner wall surfaces respectively defining the indentations, and a plurality of suction holes that are in air communication with the respective indentations and that are connected to a suction device, each of the annular inner wall surfaces having an annular outer edge that meets the continuous rolling surface, the second roller having a rolling surface that is formed with a plurality of protrusion members thereon, the third roller having a rolling surface;
    (b) feeding a top sheet to pass through a first nip zone formed between the first roller and the second roller, wherein each of the protrusion members extends into one of the indentations in the first nip zone, and the top sheet is pressed by the protrusion members and is sucked to contact against the annular inner wall surfaces through the suction holes and the suction device so that the top sheet is formed with a plurality of projection portions corresponding to the indentations of the first roller, and a plurality of indented annular connecting portions each surrounding one of the projection portions, the indented annular connecting portions constituting an interconnecting structure; and
    (c) subsequently feeding the top sheet together with a bottom sheet to pass through a second nip defined by the first roller and the third roller, wherein the third roller is heated so that the top sheet and the bottom sheet are melt bonded to each other between the rolling surfaces of the first and third rollers.

2. The method as claimed in claim 1, wherein said annular outer edge of each of the annular inner wall surfaces has a hexagonal shape.

3. The method as claimed in claim 1, wherein said annular outer edge of each of the annular inner wall surfaces has an octagonal shape.

4. The method as claimed in claim 1, further comprising:
    providing a heated fourth roller having a rolling surface that is formed with a plurality of spaced-apart pins, and a fifth roller in rolling contact with the fourth roller and having an elastic rolling surface; and
    feeding the top and bottom sheets, which have been bonded to each other, to pass through a third nip zone defined by the fourth roller and the fifth roller, wherein the pins extend into the top and bottom sheets to form a plurality of pin holes in the indented annular connecting portions.

* * * * *